United States Patent
Kato et al.

(10) Patent No.: US 10,307,859 B2
(45) Date of Patent: Jun. 4, 2019

(54) JOINT PART DETERMINATION METHOD AND JOINT MATERIAL MANUFACTURING METHOD

(71) Applicant: Mitsubishi Heavy Industries Engineering, Ltd., Yokohama-shi, Kanagawa (JP)

(72) Inventors: Yoshinori Kato, Tokyo (JP); Kazushige Yamasu, Tokyo (JP)

(73) Assignee: MITSUBISHI HEAVY INDUSTRIES ENGINEERING, LTD., Yokohama-Shi, Kanagawa (JP)

( * ) Notice: Subject to any disclaimer, the term of this patent is extended or adjusted under 35 U.S.C. 154(b) by 0 days.

(21) Appl. No.: 15/516,831

(22) PCT Filed: Sep. 9, 2015

(86) PCT No.: PCT/JP2015/075591
§ 371 (c)(1),
(2) Date: Apr. 4, 2017

(87) PCT Pub. No.: WO2016/056341
PCT Pub. Date: Apr. 14, 2016

(65) Prior Publication Data
US 2017/0266754 A1    Sep. 21, 2017

(30) Foreign Application Priority Data
Oct. 10, 2014 (JP) .................. 2014-208813

(51) Int. Cl.
*B23K 20/12* (2006.01)
*B23K 31/12* (2006.01)
(Continued)

(52) U.S. Cl.
CPC .......... *B23K 20/12* (2013.01); *B23K 20/1265* (2013.01); *B23K 31/125* (2013.01);
(Continued)

(58) Field of Classification Search
CPC .. B23K 20/12; B23K 20/1265; B23K 31/125; G01N 29/043; G01N 29/06; G01N 29/44; G01N 29/4445
See application file for complete search history.

(56) References Cited

U.S. PATENT DOCUMENTS

2007/0282543 A1    12/2007   Hiyama et al.
2009/0140026 A1     6/2009   Okauchi et al.
(Continued)

FOREIGN PATENT DOCUMENTS

JP   H06-265529 A    9/1994
JP   2005-315582 A   11/2005
(Continued)

OTHER PUBLICATIONS

PCT/ISA/210, "International Search Report for International Application No. PCT/JP2015/075591," dated Nov. 24, 2015.
(Continued)

*Primary Examiner* — David Z Huang
(74) *Attorney, Agent, or Firm* — Manabu Kanesaka; Benjamin Hauptman; Kenneth Berner

(57) ABSTRACT

A method includes the following: an incidence step in which ultrasonic waves from an insertion side and the side opposite thereto of a tool are caused to be incident on a joint part when a workpiece is joined by the tool that has a probe and a shoulder which supports the probe and that is for friction stir welding; an image acquisition step for obtaining an ultrasonic wave transmission image of the joint part using the ultrasonic waves; and a determination step for determining that the joint part has been joined if width-dimensions of the joint part obtained from the ultrasonic wave transmission image are equivalent to at least the outer diameter d of the probe and if no defect of a prescribed size or greater is found in a range equivalent to the outer diameter D of the shoulder or less in the ultrasonic wave transmission image.

6 Claims, 2 Drawing Sheets

(51) Int. Cl.
  *G01N 29/04* (2006.01)
  *G01N 29/44* (2006.01)
  *G01N 29/06* (2006.01)
  *B23K 31/00* (2006.01)
(52) U.S. Cl.
  CPC .......... *G01N 29/043* (2013.01); *G01N 29/06* (2013.01); *G01N 29/44* (2013.01); *G01N 29/4445* (2013.01); *B23K 31/003* (2013.01); *G01N 2291/267* (2013.01)

(56) References Cited

U.S. PATENT DOCUMENTS

2012/0125522 A1   5/2012   Kato et al.
2012/0310551 A1   12/2012  Na et al.

FOREIGN PATENT DOCUMENTS

| JP | 2013-047646 A | 3/2013 |
|---|---|---|
| KR | 10-2008-0110893 A | 12/2008 |
| WO | 2007/116629 A1 | 10/2007 |
| WO | 2011/086602 A1 | 7/2011 |

OTHER PUBLICATIONS

PCT/ISA/237 "Written Opinion of the International Searching Authority for International Application No. PCT/JP2015/075591," dated Nov. 24, 2015.
Lamarre, A. et al., "Ultrasound Phased Array Inspection Technology for the Evaluation of Friction Stir Welds," Friction Stir Welding, Jun. 26-28, 2000, p. 1-15.

JOINT PART DETERMINATION METHOD AND JOINT MATERIAL MANUFACTURING METHOD

TECHNICAL FIELD

The present invention relates to a joint part determination method which is performed after a workpiece is joined by friction stir welding and a joint material manufacturing method including this determination method.

Priority is claimed on Japanese Patent Application No. 2014-208813, filed on Oct. 10, 2014, the content of which is incorporated herein by reference.

BACKGROUND ART

As a method of joining a workpiece including two members, friction stir welding is known. The friction stir welding is a method which joins a workpiece using friction heat generated on a workpiece surface by rotating a tool in a state where a joint part of the workpiece is pressurized by a shoulder surface of the tool.

Meanwhile, in the related art, inspection of a joined state is performed on the joint part of the friction stir welding by Ultrasonic Testing (UT) after the joining.

In the Ultrasonic Testing, it is possible to inspect internal defects or a joint diameter disclosed in PTL 1, for example. It is possible to prevent a pressure-joint surface region from being misidentified as a diffusion joint region and accurately measure a diffusion joint diameter by using the method of PTL 1.

CITATION LIST

Patent Literature

Japanese Unexamined Patent Application Publication No. 2013-47646

SUMMARY OF INVENTION

Technical Problem

However, since the joint diameter is estimated based on a distance ΔT with a rear surface of a member to be joined in the method disclosed in PTL 1, the joint diameter is not an actual measurement value. Accordingly, determination whether or not the joined state is sufficient is not performed based on the actual measurement value and is performed based on the estimated value, it may be impossible to secure a sufficient joint quality.

The present invention provides a joint part determination method which determines a joined state of a joint part by a simple method to improve a joint quality, and a joint material manufacturing method including this determination method.

Solution to Problem

According to a first aspect of the present invention, there is provided a joint part determination method, including: an incidence step of causing ultrasonic waves to be incident to a joint part from a side opposite to an insertion side of a probe in the joint part when a workpiece formed by stacking members is joined by a tool for friction stir welding which includes the probe which is inserted into the workpiece and a shoulder which supports the probe; an image acquisition step of obtaining an ultrasonic wave transmission image of the joint part by the ultrasonic waves; and a determination step of determining that the joint part is joined in a case where a width dimension of the joint part obtained by the ultrasonic wave transmission image is equal to or more than an outer diameter of the probe and in no joint defect of a predetermined size or more is found within a range equal to or less than an outer diameter of the shoulder in the ultrasonic wave transmission image.

If ultrasonic waves are incident to the joint part, the ultrasonic waves are not reflected from a part in which the joining is being performed, and the part is acquired as the ultrasonic wave transmission image. At this time, a pressure joint part (a part in which the joining is insufficiently performed and members are pressure-joined) in which the joining is insufficient may be considered as a part in which the joining is being performed. In this case, the width dimension of the joint part obtained by the ultrasonic wave transmission image includes the pressure joint part, and a range which is larger than the outer diameter of the probe is acquired as the ultrasonic wave transmission image.

Here, since the workpiece is stirred at a position through which the probe passes, if the width dimension of the joint part obtained by the ultrasonic wave transmission image is equal to or more than the outer diameter of the probe, it can be regarded that the joining is firmly performed within at least the range of the outer diameter of the probe. In addition, if the joining is performed within the range of the outer diameter of the probe, in a case where the size of the joint defect within the range equal to or less than the outer diameter of the shoulder is suppressed to a predetermined value, it can be said that joining strength can be maintained.

In the present invention, the size of the joint defect within the range equal to or less than the outer diameter of the shoulder is determined from the ultrasonic wave transmission image, and it is possible to detect whether or not the size of the joint defect within this range is suppressed to the predetermined value. Accordingly, as described above, it is possible to easily determine whether or not the joined state is good, based on the detection result.

Moreover, in the joint part determination method according to a second aspect of the present invention, in the determination step according to the first aspect, it may be determined that the joint part is joined in a case where no joint defect of a predetermined size or more is found within a range which is equal to or more than the outer diameter of the probe in the ultrasonic wave transmission image and is equal to or less than the outer diameter of the shoulder.

The size of the joint defect within the range which is equal to or more than the outer diameter of the probe and is equal to or less than the outer diameter of the shoulder is determined from the ultrasonic wave transmission image, and it is possible to detect whether or not the size of the joint defect within this range is suppressed to a predetermined value. Accordingly, it is possible to easily determine whether or not the joined state is good, based on the detection result.

Moreover, in the joint part determination method according to a third aspect of the present invention, in the determination step according to the first or second aspect, it may be determined that the joint part is joined in a case where the maximum dimension of the joint defect when the joint defect is viewed in a direction intersecting an insertion direction of the probe is 0.2 time or less of a plate thickness of the member of the workpieces on the insertion side of the probe.

"0.2 times or less" is a numerical value which is defined in ISO25239-5:2011, and if it is possible to suppress the maximum dimension of the joint defect to 0.2 times or less of the plate thickness of the workpiece in the determination step, it can be regarded that the joined state of the joint part is good.

In addition, the maximum dimension of the joint defect when viewed in the direction intersecting the insertion direction of the probe means the maximum dimension when a cross section of the workpiece intersecting a joint direction in which the tool advances is viewed, and is not the maximum dimension in the direction along the joint direction.

In addition, in the joint part determination method according to a fourth aspect of the present invention, in the incidence step according to any one of the first to third aspects, the ultrasonic waves may be incident to the surface of the workpiece at an incident angle of 0°.

In this way, by setting the incident angle of the ultrasonic wave to 0°, whether or not the joint part of the workpiece becomes a pressure joint surface or whether or not stir welding is performed is easily detected. That is, it is possible to more correctly detect information of the joint width of the joint part from the ultrasonic wave transmission image.

Moreover, in the joint part determination method according to a fifth aspect of the present invention, the determination step according to any one of the first to fourth aspects may include a correction step of correcting the size of the joint defect obtained from the ultrasonic wave transmission image using a ratio between the outer diameter of the probe and an inner diameter of a drawing-out hole of the probe in the workpiece obtained from the ultrasonic wave transmission image.

The size or the shape of the drawing-out hole of the probe is approximately the same as the size or the shape of the probe. Accordingly, it is possible to more correctly obtain the information of the size of the joint defect by correcting the size of the joint defect acquired from the ultrasonic wave transmission image from the ratio between the actual outer diameter of the probe and the inner diameter of the drawing-out hole obtained from the ultrasonic wave transmission image. Therefore, it is possible to more correctly determine whether or not the joined state is good.

In addition, according to a sixth aspect of the present invention, there is provided a joint material manufacturing method of a joint part, including: a joining step of joining a workpiece formed by stacking members using friction stir welding; and a determination method according to any one of the first to fifth aspects which is applied to a joint part after the workpiece is joined.

According to the joint material manufacturing method, since the method includes the determination method, whether or not the size of the joint defect within the range equal to or less than the outer diameter of the shoulder is suppressed to the predetermined value can be detected. Moreover, it is possible to easily determine whether or not the joined state is good based on the detection result.

Advantageous Effects of Invention

According to the joint part determination method and the joint material manufacturing method, it is possible to determine the joined state of the joint part by a simple method, and it is possible to improve a joint quality.

DESCRIPTION OF EMBODIMENTS

Figure 1:
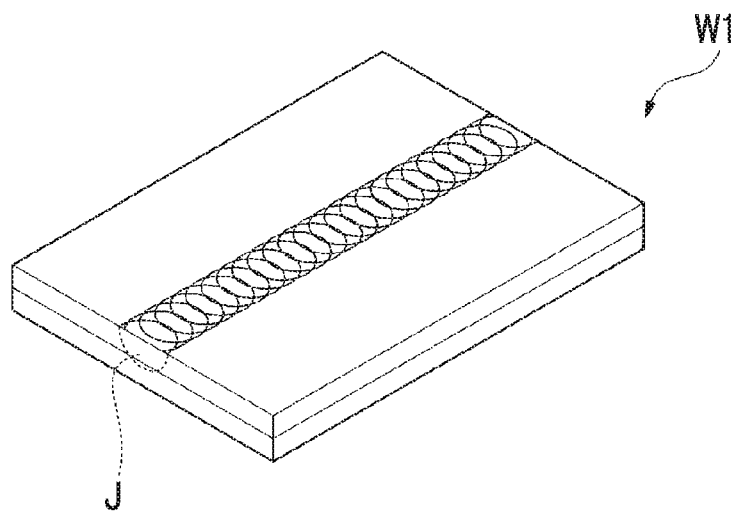
FIG. 1 is a perspective view showing a joint material which is manufactured by a joint material manufacturing method according to an embodiment of the present invention.
Figure 2:
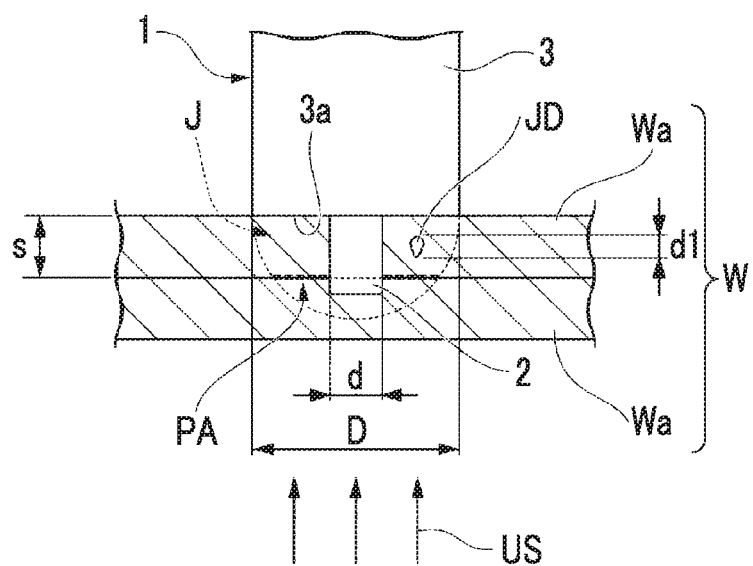
FIG. 2 is a view showing a cross section orthogonal to a workpiece surface showing a state where a determination method included in the joint material manufacturing method according to the embodiment of the present invention is performed.

Hereinafter, a manufacturing method of a joint material W1 including a joint part determination method according to an embodiment of the present invention will be described with reference to FIGS. 1 and 2.

The manufacturing method the joint material W1 is used when friction stir welding is performed on a workpiece W formed by stacking two plate members Wa (member) in a plate thickness direction so as to manufacture the joint material W1, and determines a state of a joint part J on which the friction stir welding is performed.

Figure 3:
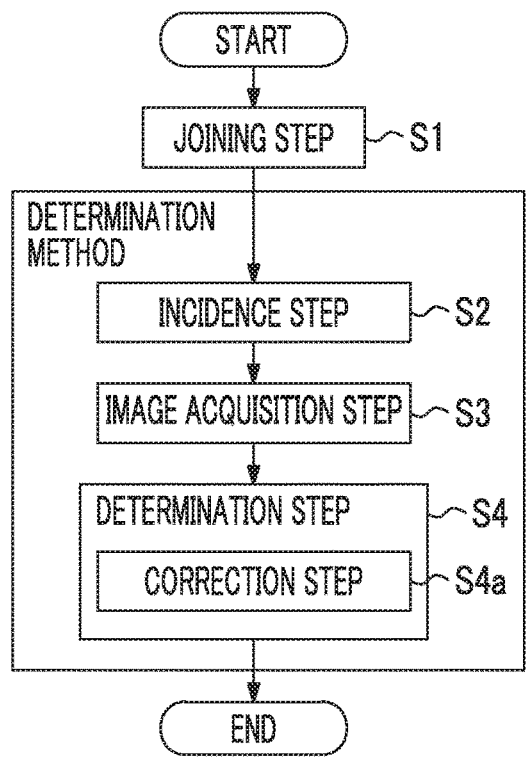
FIG. 3 is a flowchart showing the joint material manufacturing method according the embodiment of the present invention.

Specifically, as shown in FIG. 3, the manufacturing method of the joint material W1 includes a joining step S1 of performing the friction stir welding on the workpiece W to achieve joining of the workpiece W, and a determination method including a step of determining a state of the joint part J of the workpiece W after the joining.

First, the joining step S1 is performed. In the joining step S1, a tool 1 for friction stir welding approaches the workpiece W from one side in a stacking direction of the workpiece W which is the plate thickness direction of the plate member Wa, the tool 1 rotates while pressing the surfaces of the plate member Wa so as to generate a plastic flow of the workpiece W, and the workpiece is joined.

Here, the tool 1 for friction stir welding includes a probe 2 which is formed in a bar shape and is inserted from the surface of the workpiece W into the workpiece W during the joining, and a shoulder 3 which is formed in a bar shape, supports one end of the probe 2, has a larger diameter than that of the probe 2, and includes a shoulder surface 3a which is pressed to the surface of the plate member Wa during the joining.

Next, the determination method of the joint part J is performed.

The determination method includes an incidence step S2 of causing ultrasonic waves US to be incident, an image acquisition step S3 of obtaining an ultrasonic wave transmission image by the incident ultrasonic waves US, and a determination step S4 of determining the state of the joint part J from the ultrasonic wave transmission image.

First, in the determination method, the incidence step S2 is performed. That is, the ultrasonic waves US are incident to the joint part J from the other side of the joint part J of the workpiece W in the plate thickness direction, that is, a side opposite to the side of the joint part J on which the tool 1 is pressed to the plate member Wa.

Here, as a method of inspecting the joint part J, in general, a method referred to as Ultrasonic Testing (UT) is known. The Ultrasonic Inspection is a type of non-destruction testing. In the Ultrasonic Testing, when ultrasonic wave pulses are transmitted to the joint part, it is possible to specify the size or position of a joint defect by preparing and confirming an image from reflective waves which are reflected by the joint defect inside the joint part. A part through which the ultrasonic waves are transmitted without being reflected can be regarded as a part which is being joined, and it is possible to acquire information indicating this part as the ultrasonic wave transmission image.

Next, the image acquisition step S3 is performed. That is, the ultrasonic wave transmission image is acquired as the information of the part through which the incident ultrasonic waves US are transmitted. In the present embodiment, the ultrasonic waves US are incident in a direction orthogonal to the surface of the plate member Wa. That is, the ultrasonic waves US are incident at an incident angle 0° with respect to the surface.

Here, when the ultrasonic wave transmission image is acquired by the ultrasonic waves US, as described above, the ultrasonic waves US are not reflected from the part in which the joining is being performed, and the part is acquired as the ultrasonic wave transmission image. At this time, a pressure joint part PA (a part in which the joining is insufficiently performed and members are pressure-joined, refer to FIG. 2) in which the joining is insufficient may be considered as a part in which the joining is being performed. In this case, a width dimension of the joint part J obtained by the ultrasonic wave transmission image includes the pressure joint part PA, and a range which is larger than an outer diameter d of the probe 2 is acquired as the ultrasonic wave transmission image.

The width dimension of the joint part J is a dimension in a direction orthogonal to the joint direction in which the tool 1 advances and the plate thickness direction of the plate member Wa.

Finally, the determination step S4 is performed. That is, it is determined that the joint part J is joined in a case where the width dimension of the joint part J obtained by the ultrasonic wave transmission image is equal to or more than the outer diameter d of the probe 2, and no joint defect JD of a predetermined size or more is found within a range equal to or more than the outer diameter d of the probe 2 and equal to or less than an outer diameter D of the shoulder 3 in the ultrasonic wave transmission image, and the manufacturing of the joint material W1 is completed.

In the present embodiment, it is determined that the joint part J is joined in a case where a diameter d1 of the joint defect JD determined by the determination step S4 is equal to or less than 0.2 times of a plate thickness s of the plate member Wa of the workpiece W on the insertion side of the probe 2. That is, $d1 \leq 0.2\ s$ is established. The value of this expression is a numerical value which is defined by "ISO25239-5:2011".

The diameter d1 of the joint defect JD indicates the maximum dimension of the joint defect JD when the joint defect JD is viewed in the direction (may be the direction intersecting) orthogonal to the plate thickness direction (the insertion direction of the probe 2) of the workpiece W, and corresponds to a long diameter in a case where the joint defect JD is formed in an elliptic shape.

That is, the maximum dimension of the joint defect JD means the maximum dimension when the cross section of the workpiece W orthogonal to the joint direction is viewed, and is not the maximum dimension in the direction along the joint direction.

In addition, the determination step S4 includes a correction step S4a of correcting the size of the joint defect JD obtained from the ultrasonic wave transmission image using a ratio between the outer diameter d of the probe 2 and an inner diameter of a drawing-out hole of the probe 2 in the workpiece W obtained from the ultrasonic wave transmission image.

In the friction stir welding, after the joining, it is necessary to draw out the probe 2 inserted into the workpiece W, and the drawing-out hole is formed when the probe 2 is drawn out.

According to the manufacturing method of the joint material W1, the size of the joint defect JD within the range equal to or more than at least the outer diameter d of the probe 2 and equal to or less than the outer diameter D of the shoulder 3 is determined from the ultrasonic wave transmission image by performing the determination method of the joint part J, and presence or absence of the joint defect JD having a predetermined size can be detected at this position.

Here, the workpiece W is stirred at the position through which the probe 2 passes. Accordingly, if the width dimension of the joint part obtained by the ultrasonic wave transmission image is equal to or more than the outer diameter d of the probe 2, it can be regarded that the joining is firmly performed within the range of at least the outer diameter d of the probe 2.

In addition, in the case where the joining is performed within the range of the outer diameter d of the probe 2, if the size of the joint defect JD within a range equal to or more than the outer diameter d of the probe 2 and equal to or less than the outer diameter D of the shoulder 3 is suppressed to a predetermined value, it can be said that joining strength can be maintained.

Accordingly, in the present embodiment, in this way, whether or not the size of the joint defect JD within a range equal to or more than the outer diameter d of the probe 2 and equal to or less than the outer diameter of the shoulder 3 is suppressed to a predetermined value is detected, and it is possible to easily determine whether or not the joined state is good, based on the detection result.

Moreover, by setting whether or not the size of the joint defect satisfies $d1 \leq 0.2\ s$ to a determination reference regarding whether or not the joined state is good, it is possible to further improve the joined state of the joint part J.

Figure 4:
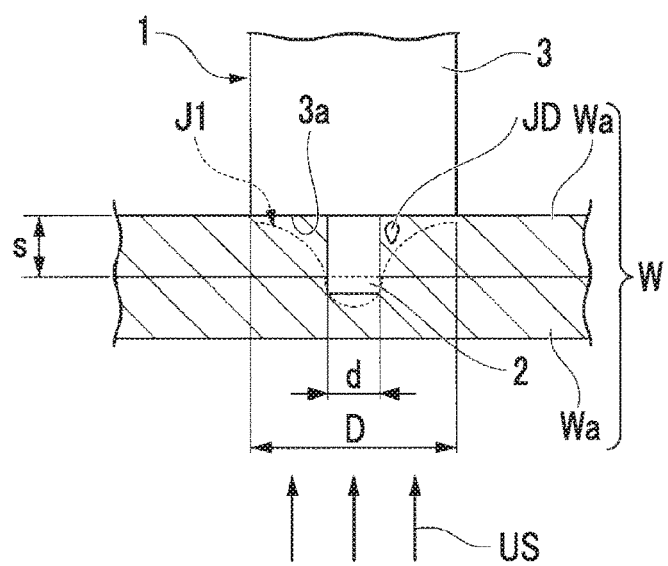
FIG. 4 is a view showing the cross section orthogonal to the workpiece surface showing another example of the state where the determination method included in the joint material manufacturing method according to the embodiment of the present invention is performed.

Here, as shown in FIG. 4, when the friction stir welding is performed, a joint part J1 has a shape along the outer surface of the probe 2, and a joint defect JD (void) may occur at a position close to the probe 2 on the outside in the radial direction of the probe 2. In this case, particularly, joining strength of the joint part J1 decreases. However, in the present embodiment, it is possible to cause the joined state to be good by performing the joint part determination method.

In addition, by setting the incident angle of the ultrasonic wave US to 0°, whether or not the joint part J of the workpiece W becomes the pressure joint surface PA or whether or not stir welding is performed is easily detected. Accordingly, it is possible to more correctly detect information of the width dimension of the joint part J from the ultrasonic wave transmission image.

Moreover, the size or the shape of the drawing-out hole of the probe 2 is approximately the same as the size or the shape of the probe 2. Accordingly, by performing the correction step S4a in the determination step S4, it is possible to more correctly obtain the information of the size of the joint defect JD by correcting the size of the joint defect JD acquired from the ultrasonic wave transmission image from the ratio between the actual outer diameter d of the probe and the inner diameter of the drawing-out hole obtained from the ultrasonic wave transmission image. Therefore, it is possible to more correctly determine whether or not the joined state is good.

According to the manufacturing method of the joint material W1 of the present embodiment, since the above-described determination method is used, it is possible to determine the joined state by a simple method, and it is possible to improve a joint quality of the joint material W1.

Hereinbefore, the embodiment of the present invention is described in detail. However, some design modifications may be applied within a scope which does not depart from a technical idea of the present invention.

For example, in the above-described embodiment, the incident angle of the ultrasonic wave US is set to 0°. However, the present invention is not limited to this. For example, the ultrasonic wave US can be incident at the incident angle of 45°. In this case, in a case where the joint defect JD extending the plate thickness direction exists in the joint part J (J1), the joint defect is easily found.

In addition, in the determination step S4, it is not necessarily perform the correction step S4a.

Moreover, the above-described determination method can be applied to friction stir spot welding. In addition, in this friction stir spot welding, the tool 1 moves to the position separated from the joint part along the surface of the workpiece W after the joining is performed such that the drawing-out hole of the probe 2 is not formed in the joint part, and thereafter, the probe 2 is drawn out.

Moreover, in the determination step S4, it may be determined that the joint part J is joined in a case where no joint defect JD having a predetermined size is found within the range equal to or less than the outer diameter D of the shoulder 3 in at least the ultrasonic wave transmission image. That is, the determination may not be necessarily performed based on presence or absence of the joint defect JD within the range equal to or more than the outer diameter d of the probe 2 and equal to or less than the outer diameter D of the shoulder 3.

In addition, in the determination step S4, the present invention is not limited to the case where it is determined that the joint part J is joined when the diameter d1 of the joint defect JD is equal to or less than 0.2 s, and it may be determined that the joint part J is joined in a case where the diameter d1 is equal to or less than 4 mm.

Moreover, in the above-described manufacturing method, instead of the above-described tool 1, a bobbin tool can be used, which includes two shoulders (upper shoulder and lower shoulder) supporting the probe 2 from both ends and in which joining is performed in a state where the workpiece W is interposed between the two shoulders. In this case, the ultrasonic waves US may be incident to the joint part from any one of one side or the other side in the plate thickness direction of the joint part.

In addition, the member configuring the workpiece W is not limited to the case of being the plate member, and the member may be members which are at least stacked so as to be joined by friction stir welding, for example, may be extrusion-shaped materials, or the like.

INDUSTRIAL APPLICABILITY

According to the joint part determination method and the joint material manufacturing method, it is possible to determine the joined state of the joint part by a simple method, and it is possible to improve a joint quality.

REFERENCE SIGNS LIST

1: tool
2: probe
3: shoulder
3a: shoulder surface
W1: joint material
W: workpiece
Wa: plate member (member)
PA: pressure joint part
J, J1: joint part
JD: joint defect
US: ultrasonic wave
S1: joining step
S2: incidence step
S3: image acquisition step
S4: determination step
S4a: correction step

The invention claimed is:

1. A joint part determination method, comprising:
an incidence step of causing ultrasonic waves to be incident to a joint part from a side opposite to an insertion side of a probe in the joint part when a workpiece formed by stacking members is joined by a tool for friction stir welding which includes the probe which is inserted into the workpiece and a shoulder which supports the probe;
an image acquisition step of obtaining an ultrasonic wave transmission image of the joint part by the ultrasonic waves; and
a determination step of determining that the joint part is joined in a case where a width dimension of the joint part obtained by the ultrasonic wave transmission image is equal to or more than an outer diameter of the probe and no joint defect of a predetermined size or more is found within a range equal to or less than an outer diameter of the shoulder in the ultrasonic wave transmission image.

2. The joint part determination method according to claim 1,
wherein in the determination step, it is determined that the joint part is joined in a case where no joint defect of the predetermined size or more is found within a range which is equal to or more than the outer diameter of the probe in the ultrasonic wave transmission image and is equal to or less than the outer diameter of the shoulder.

3. The joint part determination method according to claim 1,
wherein in the determination step, it is determined that the joint part is joined in a case where the maximum dimension of the joint defect when the joint defect is viewed in a direction intersecting an insertion direction of the probe is 0.2 times or less of a plate thickness of the member of the workpieces on the insertion side of the probe.

4. The joint part determination method according to claim 1,
wherein in the incidence step, the ultrasonic waves are incident to a surface of the workpiece at an incident angle of 0°.

5. The joint part determination method according to claim 1,
wherein the determination step includes a correction step of correcting a size of the joint defect obtained from the ultrasonic wave transmission image using a ratio between the outer diameter of the probe and an inner diameter of a drawing-out hole of the probe in the workpiece obtained from the ultrasonic wave transmission image.

6. A joint material manufacturing method, comprising:
a joining step of joining a workpiece formed by stacking members using friction stir welding; and
the joint part determination method according to claim 1 which is applied to a joint part after the workpiece is joined.

* * * * *